United States Patent [19]

Faste

[11] Patent Number: 4,898,582
[45] Date of Patent: Feb. 6, 1990

[54] PORTABLE INFUSION DEVICE ASSEMBLY

[75] Inventor: Rolf A. Faste, Stanford, Calif.

[73] Assignee: Pharmetrix Corporation, Menlo Park, Calif.

[21] Appl. No.: 230,620

[22] Filed: Aug. 9, 1988

[51] Int. Cl.⁴ .............................................. A61M 5/14
[52] U.S. Cl. ................................... 604/141; 604/151; 604/892.1; 128/DIG. 12
[58] Field of Search .................. 604/891.1, 892.1, 896, 604/131, 141, 151, 93, 244; 128/DIG. 12

[56] References Cited

U.S. PATENT DOCUMENTS 4,511,355  4/1985  Franetski et al. ............... 604/891.1
4,552,561  11/1985  Eckenhoff et al. .............. 604/891.1
4,689,044  8/1987  Murata ............................. 604/306

Primary Examiner—Stephen C. Pellegrino
Attorney, Agent, or Firm—A. J. Castro; J. Farrant

[57] ABSTRACT

A portable infusion device assembly, having two side-by-side compartments, the first containing the drug or agent to be infused and an osmotic pump, and the second containing the driving liquid for the pump. The two chambers are separated during storage by a barrier. When the barrier is ruptured, the driving fluid is carried by means of a wick to the osmotic pump. The drug is then forced out of the device by the pressure developed by the osmotic pump. The assembly is characterized by a very flat profile, and is light, comfortable, and inconspicuous in use.

8 Claims, 2 Drawing Sheets

PORTABLE INFUSION DEVICE ASSEMBLY

FIELD OF THE INVENTION

This invention relates to controlled release infusion devices, and particularly to small body-mounted devices capable of delivering drugs or other pharmaceutical agents for prolonged periods.

BACKGROUND OF THE INVENTION

Many kinds of parenteral drug therapy require continuous delivery in preference to single or multiple injections. Benefits that accrue from continuous therapy may include, for instance, reduction of toxic or other side effects associated with sharp pulses of drug, significant improvement in the effectiveness of the therapy, and increased comfort of the patient. The traditional manner of administering sustained parenteral treatments is an intravenous drip. While this may be perfectly acceptable in a hospital environment, it obviously imposes severe restrictions on the activity of the recipient. As a result, considerable research over the last few years has been devoted to the development of small portable infusion pumps. A range of devices has appeared, including those with electric or clockwork motors that drive syringe or peristaltic pumps, and others powered by the elastic tension of an inflated balloon, or the vapor pressure of a volatile propellant. Literature incorporated herein by reference describing such pumps includes Controlled Release Micropump for Insulin Administration, (M. V. Sefton et al., Ann. Biomed. Eng., Vol 7, pp. 329-343, 1979), Continuous Intravenous Arabinosyl Cytosine Infusions Delivered by a New Portable Infusion System, (J. Bottino et al., Cancer, Vol. 43, pp. 2197-2201, 1979), or product brochures from Auto-Syringe, Inc., Hooksett, N.H. and Cormed, Inc., Medina, N.Y. These devices are typically strapped to the wearer, or carried on a belt or in a harness. Also, most are designed to deliver relatively large quantities of fluid and do not dispense small volumes of the order of a few milliliters or less effectively.

An alternative approach that has been exploited to a limited extent is to drive the infusor osmotically, using a Rose-Nelson pump activated by imbibition of water or other driving liquid. In comparison with mechanically driven devices, Rose-Nelson pumps are small, reliable, and simple and cheap to manufacture. U.S. Pat. No. 3,604,417 discloses a modification of the Rose-Nelson pump in which a moveable piston replaces the elastic diaphragm separating the drug and salt chamber, and both the drug and salt are loaded into the pump as solutions. U.S. Pat. No. 4,474,048 discloses another modification employing an impermeable elastic wall, and a moveable end wall which can be screwed in to deliver a pulse dose of the contained drug at any time during the operation of the pump. U.S. Pat. No. 4,474,575 is a variant of 4,474,048 where the flow rate of the dispensed agent can be varied by altering the area of semipermeable membrane exposed to the water chamber. U.S. Pat. No. 4,552,561 discloses a pump assembly for use with a small osmotic pump, which can be filled in advance of use with the active agent to be dispensed. The action of the pump is initiated by filling the lower chamber of the housing with a hydrogel. Once the pump is in action, an optional mechanism for delivering pulse doses can be employed. All these osmotic pumps are self driven and begin to operate as soon as they are primed with the contents of the several chambers. U.S. patent application No. 892,991 commonly owned with the present application and incorporated herein by reference in its entirety, describes a portable osmotic infusion pump that can be filled with the agent to be dispensed, the osmotic salt and the driving fluid, and then stored until required.

In developing a portable infusion device, there are patient compliance as well as technical problems to be addressed. For long term infusion therapy to be successful, the infusion device must be acceptable to the wearer. Devices that are bulky, heavy, uncomfortable or obtrusive, or that cause embarrassment, or otherwise limit the user's lifestyle, or that require complicated procedures to set up or monitor, are poorly accepted. Many of the devices described above, which typically weigh up to 1 lb, and have a base area of 10-20 square inches, suffer from these inherent problems. Even the smaller units have rigid housings, and are normally carried in a belt, cuff or vest. Thus there still exists a longstanding need for comfortable, compact, discreet devices that do not obtrude on the user's lifestyle or appearance.

SUMMARY OF THE INVENTION

The present invention provides a portable controlled release infusion pump assembly. The assembly includes a housing with two side-by-side compartments. The dimensions of the housing will vary according to the amounts of drug, driving liquid, etc. that are contained, but in general the assembly is characterized by a very flat profile when compared with other infusion devices. This makes it easy to conceal under normal clothing, and represents a major advantage in terms of patient comfort and acceptability. One compartment of the housing contains an osmotic pump, consisting of a semipermeable membrane and an expandable diaphragm separated by an osmotic salt. The other compartment contains the driving liquid for the pump. The two compartments are connected by a wick. During manufacture and storage of the device the wick is separated from the driving liquid by an impermeable seal. The assembly also includes an activator that ruptures the seal, thereby allowing the driving liquid to be absorbed into the wick. The other end of the wick is in contact with the semipermeable membrane. When the infusor is in use, liquid travels through the wick and contacts the semipermeable membrane. The liquid diffuses through the membrane under a concentration gradient, creating a saturated salt solution, and exerting a pressure on the expandable diaphragm, which in turn forces the agent to be dispensed out of the assembly through a delivery tube. The osmotic pressure developed by this type of pump is much higher than the pressure required to pump the drug from the device; hence the drug delivery rate remains constant as long as some excess undissolved salt remains. The pump is extremely simple, and once activated, is self sustaining, thus problems associated with with mechanical failure, adjustment or monitoring are eliminated.

Because they are simple and small, osmotic pumps are inherently suitable for delivering small drug volumes. The pump assembly of this invention, while it can be tailored for a range of drug volumes and dosage rates, is particularly useful where the total drug volume to be dispensed is of the order of a few milliliters, and the delivery time for that volume is a day or more. Thus the invention enables therapy involving highly potent substances, such as powerful analgesics, antidotes to chemical or biological poisons, and peptide drugs of various kinds, to be carried out without subjecting the victim to repeated injections or requiring him to be hooked up to an IV drip.

The pump has no moving parts, and does not require a rigid assembly. Therefore, the pump housing may be formed from a flexible material that conforms to body contours and body movement, another major advantage as far as comfort and minimal interruption with regular activities is concerned. When filled, the pump assembly typically weighs about 10 to 20 grams. The assembly can be attached to the body of the wearer by an adhesive coating on the base of the assembly, or by adhesive strips or overlays, and does not require the use of straps, belts or other carrying garments.

The assembly can be filled with its several ingredients, stored for prolonged periods of months or years without deterioration, and activated on demand by the user.

It is an object of the present invention then to provide a portable infusion device that is readily acceptable to users.

It is another object of the invention to provide a portable infusion device that is comfortable to wear.

It is another object of the invention to provide a portable infusion device that is small and light.

It is another object of the invention to provide a portable infusion device that is inconspicuous in use.

It is another object of the invention to provide a portable infusion device that is simple to operate.

It is another object of the invention to provide a portable infusion device that is not susceptible to mechanical failure.

It is another object of the invention to provide a portable infusion device that can dispense small volumes of active agent over a prolonged period.

It is another object of the invention to provide a portable infusion device that can be prefilled with all components, and activated on demand.

Other objects and advantages of the invention will be apparent to those of ordinary skill in the art from the description that follows.

DETAILED DESCRIPTION OF THE INVENTION

"Drug" as used herein broadly includes any physiologically or pharmacologically active substance for producing a localized effect at the administration site or a systemic effect at a site remote from the administration site.

Figure 1:
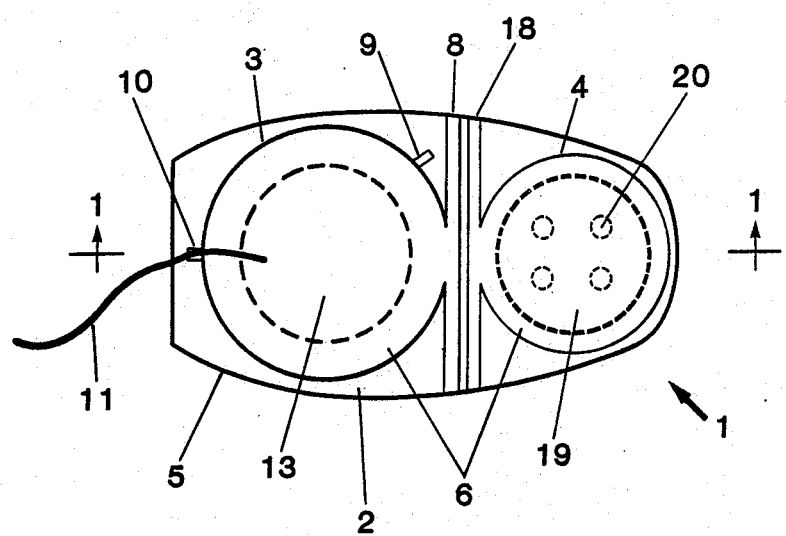
FIG. 1 is a perspective view of a basic embodiment of the invention.
Figure 2:
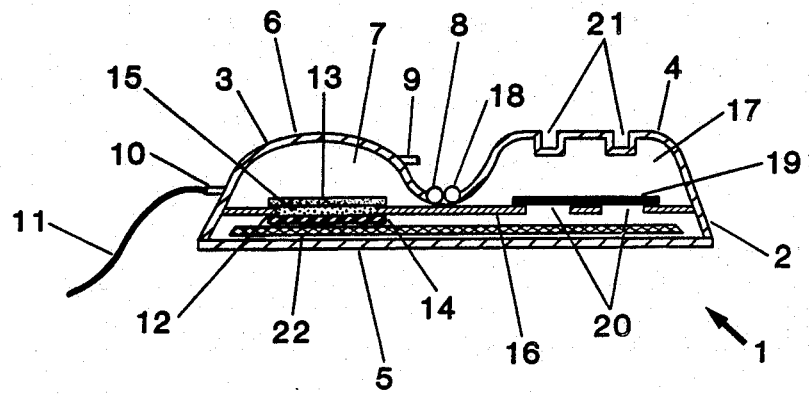
FIG. 2 is a schematic cross-section along the line 1—1.

The objects described above are achieved by an osmotic pump assembly shown in perspective view in FIG. 1, and in cross section in FIG. 2. Referring now to these figures, the pump assembly 1, has an outer housing 2, defining a first compartment 3, and a second compartment 4. The housing may be made from a rigid or non-rigid material. By non-rigid is meant sufficiently flexible to "give" to conform to body contours or movement, yet having enough structural integrity to retain the housing shape in normal use. Wherever possible, flexible materials are preferred, because they allow the device to curve to accomodate body contours. However, in some flexible embodiments, it may be desirable to provide a more rigid outer shell over either the drug or driving fluid chambers, or both, to avoid accidental compression of these compartments. In preferred embodiments, the second compartment 4, is made from a grade of material sufficiently soft to yield under atmospheric pressure as the driving liquid supply becomes exhausted, so that the pump is not working against a back pressure. The housing material should be chemically inert and impermeable to the salts, solutions and agents contained, non-irritating to the skin, acceptable for external medical use, and capable of sterilization. Materials that might be used for forming the housing include, for example, flexible or rigid grades of polyvinyl chloride, polymethylmethacrylate, or polyethylene, or polycarbonate, polysulfone or the like. The housing may be manufactured by injection or compression molding, vacuum forming or any standard technique for handling thermoplastic polymers. Alternatively, rigid embodiments may be formed from thin sheets of stainless steel, aluminum or like metal. It is generally convenient to form the housing in two parts, a flat baseplate 5, and a raised portion 6, and to join the two parts around the perimeter by heat sealing, welding or by means of an appropriate adhesive. The baseplate and the raised portion may, but need not, be made of the same material or the same grade of that material. Rigid embodiments might also be machined from lightweight, inert metal parts. In many instances it will be desirable that at least the raised portions of the housing defining the two compartments be transparent to assist the user in monitoring the status of drug or driving fluid.

The drug 7, to be dispensed, is contained within the first compartment 3. The drug may generally be any agent or combination of agents capable of administration by the parenteral route. A preferred embodiment employs a drug dissolved in an appropriate solvent, generally water. Alternatively, if the drug to be used is unstable in solution, the device can be assembled with lyophilized drug, or without drug. Water or drug solution may then be added immediately prior to use. Drugs that could be used in this way include, for example, protein or peptide drugs such as insulin, growth hormones or interferon. The pump is filled with drugs and solvents through the fill port 8, which may be placed at any convenient point on the first compartment 3. A second port 9, allows for displacement of air by the drug solution. When the pump has been filled the ports are heat sealed or otherwise closed. During use, drug leaves the device through a third port 10, and tube 11. The tube may be inserted during manufacture of the device, may be formed integrally with the housing, or may be inserted immediately before use. The end of the tube remote from the device may be adapted for use with a skin-piercing needle or a standard commercial subcutaneous drug delivery set, for example, the Sub-Q-Set ®, obtainable from Travenol Laboratories, Deerfield, Ill. Alternatively the tube may be inserted into one of the normal body orifices. Optionally one of the ports used during filling may be reopened and used as the delivery port.

The first compartment 3, also contains the osmotic pump 12, consisting of an elastic diaphragm 13, and a semipermeable membrane 14, separated by an osmotic salt 15. The delivery rate of the pump depends on the area, thickness and permeability of the semipermeable membrane. Hence the choice of a suitable membrane material is essential to good performance of the pump. A preferred choice is a membrane made from one of the cellulose esters or ethers, such as cellulose acetate or cellulose butyrate. Cellulose acetate has a long record of use in membrane applications and can easily be formed into thin films of reproducible thickness with standard solution casting techniques, making it a particularly preferred choice.

A wide range of appropriate solutes for use in osmotic pumps is disclosed in U.S. Pat. No. 4,034,756, which is incorporated herein by reference. Preferred salts are sodium chloride, potassium chloride, magnesium sulfate and sodium sulfate. These give a good range of osmotic pressure differences across the membrane and provide a means whereby the flow rate of the pump can be varied to suit the desired application.

The infusion device of the present invention can be filled, stored for extended periods of time and then activated on demand. It is, therefore, important that the elastic diaphragm be impermeable to the chosen drug, lest slow migration of drug into the salt chamber cause the device to deteriorate during storage. A wide range of standard impermeable materials with good elastomeric properties is known in the art, such as latex rubber, polyisoprene, butyl rubber, nitrile rubber, copolymers of styrene/butadiene and the like. When prolonged storage periods of months or years are envisaged, it is preferred to use a standard elastomer faced with a thin layer of aluminum foil, which will rupture as soon as the elastic diaphragm begins to expand. A second preferred alternative is to use a metallized elastic material, formed by vacuum deposition of aluminum or other metals on an elastic rubber-based material.

Manufacture is simplified if the osmotic pump is pre-assembled. This can be done by preparing a laminate by first attaching the membrane to the support member 16, typically by means of an epoxy or similar adhesive. The salt disk is then placed on top of the membrane and covered with the diaphragm, which is in turn attached to the support member by epoxy glue or otherwise. The support member may conveniently, although not necessarily, be formed from the same material as the housing and sandwiched between the upper and lower portions of the housing during manufacture.

Figure 3:
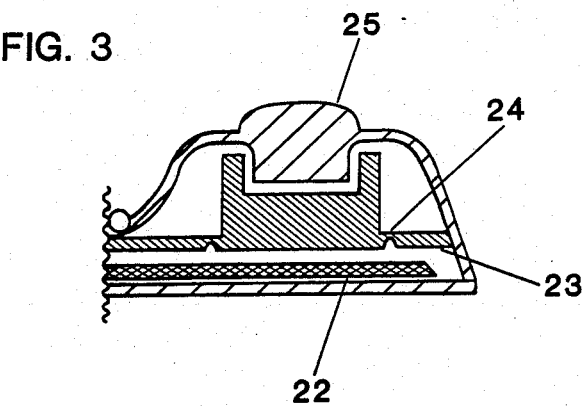
FIG. 3 is a schematic of the compartment containing the driving fluid, showing an alternative barrier and activator means.
Figure 4:
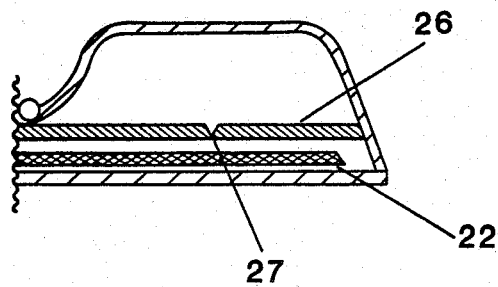
FIG. 4 is a schematic of the compartment containing the driving fluid, showing a third type of barrier and activator means.

The second compartment 4, contains the osmotic driving liquid 17. The liquid is introduced through fill port 18, which is then sealed. The driving liquid is normally water, although any liquid capable of generating an osmotic pressure in conjunction with the solute could be used. Before the pump is activated, the driving liquid is separated from the wick by an impermeable barrier. The barrier may take a number of forms. In the embodiment shown in FIGS. 1 and 2 the barrier comprises a seal 19, made from metal foil, metallized plastic film or the like, covering a hole 20, in the support member 16. This embodiment is activated by depressing the top of the second compartment so that start button 21, enters the hole 20, thereby perforating the seal and allowing the driving liquid to contact the wick 22. Other possible alternative methods of separating the driving liquid and wick, and of activating the pump, are shown in FIGS. 3 and 4. Referring now to FIG. 3, the impermeable barrier 23, has a profile as shown, and includes a ring 24, where the barrier material is comparatively thin and weak. The pump is activated by depressing the start button 25, causing the barrier to break around the ring 23. In the embodiment of FIG. 4, the impermeable barrier 26, has a radial score 27, defining a weak zone. The barrier is broken by flexing the device along the score. It should be apparent that a variety of mechanical solutions to the barrier/activation problem are possible and that the methods described are not exclusive. The invention includes the concept of a barrier and an activating device and the scope of the invention is intended to encompass any mechanism that would perform these functions.

The wick material may be filter paper, or any porous or spongy material capable of absorbing and transporting the driving liquid.

In use, the assembly of the present invention may be attached to the body of the user by means of a biocompatible adhesive applied to the baseplate, or by adhesive strips or overlays. The device may be attached anywhere on the body that is convenient, either immediately adjacent to the delivery site, or at a point distant from that site.

The following examples are given by way of illustration to further explain the principles of the invention. These examples are merely illustrative and are not to be understood as limiting the scope and underlying principles of the invention in any way.

DEVICE FABRICATION

EXAMPLE 1

The basic embodiment of the invention shown in FIGS. 1 and 2 was prepared. The housing of the device and the internal support member were fabricated from 16-mil-thick double polished polyvinyl chloride sheet. The membrane was a cellulose acetate film 25 microns thick (Clarifoil 912AA, Courtaulds CPD, Inc., Newark, N.J.). The elastic diaphragm was a Kraton ® 1652 (Shell Chemical Co., Houston, Tex.) film 40–60 microns thick, prepared by solvent casting. The osmotic salt was a disk of sodium chloride 0.03 in thick, and contained 2% Ac-Di-SOP SD-711 tablet disintegrant (FMC Corp., Philadelphia, PA). The pump sandwich, consisting of the support, diaphragm and membrane with the salt disk between, was pre-assembled with epoxy.

The device assembly was fabricated in three layers. The bottom layer was a PVC sheet on which was placed a filter paper wick approximately 1 in by 1.5 in. Another sheet of PVC, containing the membrane/salt/diaphragm subassembly, and having four 0.25-in-diameter uniformly spaced holes covered by a disk of aluminum foil, was placed on top. The top layer was vacuformed to create a drug chamber and a water chamber having a general shape as shown in FIG. 2, and tubular connections for filling the chambers and delivering the drug. Four 0.125-in draw-downs were formed in the top of the water chamber, at positions corresponding to the holes in the internal support chamber. The three PVC sheets were aligned, then joined by RF welding.

The finished pump had overall dimensions of 1.75 in by 3.4 in by 0.4 in, weighed about 7 grams empty, and had a water capacity of approximately 4 mL and a drug capacity of approximately 5 mL.

RELEASE TESTS

EXAMPLE 2

An infusion device assembly was prepared as in Example 1. The driving liquid used was water. The device was filled with a simulated drug solution comprising 2 wt% glycerol in water. The device was started and allowed to pump into a collection vessel containing 100 mL of water. The collection vessel was stirred continuously to ensure proper mixing. Samples were withdrawn periodically, and the concentration of glycerol measured by HPLC. The pumping rate was calculated from the rate of change of glycerol concentration in the collection vessel, and was found to be 0.80 mL/day.

The experiments were repeated with other batches of pumps prepared in the same way. Pumping rates of 0.82 mL/day and 0.94 mL/day were measured.

I claim:

1. A portable infusion device assembly, comprising;
   (a) a housing, defining first and second compartments disposed in side-by side relationship to one another,
   (b) an osmotic pump, disposed within said first compartment,
   (c) a driving liquid for said pump disposed within said second compartment,
   (d) wick means, disposed within said housing, in liquid transferring relationship between said first and second compartments,
   (e) a barrier disposed between said wick means and said driving liquid, and separating said driving liquid from said wick, and
   (f) means integral with said housing or said barrier for rupturing said barrier so that upon rupture of said barrier, said driving liquid will be transferred by said wick from said second compartment to said first compartment.

2. A portable infusion device, comprising;
   (a) a flexible housing, defining first and second compartments disposed in side-by side relationship to one another,
   (b) an osmotic pump, disposed within said first compartment,
   (c) a driving liquid for said pump disposed within said second compartment,
   (d) wick means, disposed within said housing, in liquid transferring relationship between said first and second compartments,
   (e) a barrier disposed between said wick means and said driving liquid, and separating said driving liquid from said wick, and
   (f) means integral with said housing or said barrier for rupturing said barrier so that upon rupture of said barrier, said driving liquid will be transferred by said wick from said second compartment to said first compartment.

3. A housing for a portable osmotic device, comprising;
   (a) a baseplate,
   (b) an upper portion designed in such a manner that side-by-side compartments are created when said upper portion is sealed to said baseplate around its perimeter,
   (c) a support means within said first compartment for holding an osmotic pump,
   (d) a wick means, disposed within said housing, in liquid transferring relationship between said first and second compartments and
   (e) sealing means for isolation said first compartment from said second compartment.

4. The housing of claim 3, wherein said baseplate is flexible.

5. The housing of claim 3, where said upper portion is of flexible construction.

6. The housing of claim 3, wherein said compartment surfaces are of flexible construction.

7. The housing of claim 3, wherein said support means and said sealing means comprise a single internal support member disposed generally parallel to said baseplate, said single internal support being sealed to said raised portion around its perimeter and between said first and second compartments.

8. A method of infusing a patient, comprising connecting said patient to a portable osmotic infusion device, said device comprising:
   (a) a housing, defining first and second compartments disposed in side-by-side relationship to one another,
   (b) an osmotic pump, disposed within said first compartment,
   (c) a driving liquid for said pump disposed within said second compartment,
   (d) wick means, disposed within said housing, in liquid transferring relationship between said first and second compartments,
   (e) a barrier disposed between said wick means and said driving liquid, and separating said driving liquid from said wick,
   (f) means integral with said housing or said barrier for rupturing said barrier so that upon rupture of said barrier, said driving liquid will be transferred by said wick from said second compartment to said first compartment,
   (g) activating said device by rupturing said barrier.

* * * * *